US00PP20613P2

(12) United States Plant Patent
Scheys

(10) Patent No.: US PP20,613 P2
(45) Date of Patent: Dec. 29, 2009

(54) ***HEUCHERA* PLANT NAMED 'BLACKOUT'**

(50) Latin Name: *Heuchera* hybrid
Varietal Denomination: Blackout

(76) Inventor: Diederik A. M. Scheys, Zavelstraat 27, Pellenberg (BE) 3212

( * ) Notice: Subject to any disclaimer, the term of this patent is extended or adjusted under 35 U.S.C. 154(b) by 58 days.

(21) Appl. No.: 12/070,777

(22) Filed: Feb. 21, 2008

(51) Int. Cl.
*A01H 5/00* (2006.01)

(52) U.S. Cl. ..... Plt./440
(58) Field of Classification Search ..... Plt./440
See application file for complete search history.

*Primary Examiner*—June Hwu
(74) *Attorney, Agent, or Firm*—Penny J. Aguirre

(57) ABSTRACT

A new cultivar of hybrid *Heuchera* named 'Blackout', characterized by its glossy, dark black-brown colored foliage held nearly flat on dark purple petioles, its compact and mounded plant habit, its vigor, and its hardiness in at least U.S.D.A Zones 4 to 9.

3 Drawing Sheets

Botanical classification: *Heuchera* hybrid.
Cultivar designation: 'Blackout'.

BACKGROUND OF THE INVENTION

The present invention relates to a new and distinct cultivar of hybrid *Heuchera*, botanically known as a *Heuchera* of hybrid origin and is hereinafter referred to by its cultivar name 'Blackout'.

The inventor discovered the new cultivar, 'Blackout', as a naturally occurring whole plant mutation in Pellenberg, Belgium in May of 2006. 'Blackout' was discovered in a trial garden that had been planted with seeds that were derived from open pollination of *Heuchera* 'Prince' (unpatented).

Asexual reproduction of the new cultivar was first accomplished under direction of the inventor by in vitro propagation in Rijswijk, The Netherlands in March of 2007. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Blackout' as a new and unique cultivar of *Heuchera*.

1. 'Blackout' exhibits unique foliage with leaves that are dark black-brown in color, darker than those of any *Heuchera* cultivar known to the inventor.
2. 'Blackout' exhibits leaves that have a glossy surface and are held nearly flat with a slight wave but lacking ruffles or curling.
3. 'Blackout' exhibits dark purple petioles.
4. 'Blackout' has a compact, mounded plant habit.
5. 'Blackout' has a more vigorous growth habit than is typical for dark foliaged *Heuchera* cultivars.
6. 'Blackout' is cold hardy at least in U.S.D.A. Zones 4 to 9.

'Blackout' differs from its parent plant, 'Prince' in having much darker foliage. 'Prince' also differs in having leaves that are more purple in color and highly ruffled.

'Blackout' can be compared to 'Obsidian' (U.S. Plant Pat. No. 14,836) and 'Black Beauty' (U.S. Plant Pat. No. 13,288) for its similarity in leaf color. In comparison to 'Obsidian', 'Blackout' has a more vigorous growth habit and leaves that is darker under various light conditions, darker when they emerge and glossier. In comparison to 'Black Beauty', 'Blackout' has leaves that are darker and less red in color. 'Black Beauty' also has ruffled leaves whereas the leaves of 'Blackout' lack ruffles.

BRIEF DESCRIPTION OF THE DRAWING

The accompanying colored photographs illustrate the overall appearance and distinct characteristics of the new *Heuchera*. The photographs were taken in mid summer in The Netherlands of plants six month in age as grown outdoors in a 3-liter container from 2 plugs.

The photograph on the first sheet provides a side view of the plant habit and typical mid summer coloration of the foliage of 'Blackout'.

The photograph on the second sheet provides a close-up view of the foliage of 'Blackout'.

The photograph on the third sheet provides a view of 'Blackout' in bloom.

The colors in the photographs are as close as possible with the photographic and printing technology utilized. The color values cited in the detailed botanical description accurately describe the colors of the new *Heuchera*.

DETAILED BOTANICAL DESCRIPTION OF THE PLANT

The following is a detailed description of a six month-old plants of the new cultivar as grown outdoors in a 3-liter container from 2 plugs in The Netherlands with flower data collected on a plant 2 years in age as grown in a garden in New Hope, Minn. Plants were grown under average day temperatures of 12° to 39° C. and average night temperatures of 5° to 16° C. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—About 3 weeks in mid summer.

*Plant habit.*—Compact, clump-forming herbaceous perennial, mounded foliage.

*Height and spread.*—Reaches a height of 20 to 30 cm in height and about 40 cm in width when mature.

*Hardiness.*—U.S.D.A. Zone 4 to 9.

*Culture.*—Full sun to medium shade in moist, well-drained, fertile soils.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Root initiation.*—Roots appear in rooting media in 10 day at 20° C. in the laboratory without supplemental lighting.

*Root development.*—Rooted transplants from tissue culture fully develop in a 2.5 inch container in about 20 days in a greenhouse with average temperatures of about 20° C. without supplemental lighting in The Netherlands.

*Growth rate.*—Moderate but more vigorous than is typical for dark foliaged *Heuchera*, growing an average of 5 cm per month in the spring, about 20 weeks is required to finish a 9 cm container from a rooted transplant.

Foliage description:

*Leaf shape.*—Orbicular.

*Leaf division.*—Simple.

*Leaf base.*—Hastate.

*Leaf apex.*—Rounded with a very small abruptly acute tip about 0.5 mm in length.

*Leaf venation.*—Palmate, 200C to 200D in color on upper surface and N77A in color on lower surface.

*Leaf margins.*—Lobed with average of 5 lobes per leaf, lobe margins crenate.

*Leaf attachment.*—Petiolate.

*Leaf arrangement.*—Basal rosettes.

*Leaf orientation.*—Held nearly horizontal to petiole, held nearly flat with slight wave.

*Leaf surface.*—Upper and lower sides are slightly glossy and pubescent, sparsely covered with white hairs 0.5 mm in length and 155C in color.

*Leaf color.*—Young upper surface; 200B, young lower surface; 187A to 187B, mature upper surface; between 200A and N200A, mature lower surface; N77C.

*Leaf size.*—Average of 7.2 cm in length and 7.0 cm in width.

*Leaf quantity.*—About 30 per plant as grown from 2 plugs in a 3-liter container.

*Petioles.*—Round in shape, average of 10.6 cm in length and 1.5 mm in width, N186C in color, surface is moderately covered with soft hairs with an average of 2 mm in length and 155C in color.

*Stipules.*—None.

Flower description:

*Inflorescence type.*—Numerous small bell-shaped flowers arranged on pyramidal panicles on flower scapes emerging from the base of the rosette, each peduncle has a terminal flowers and 2 lateral corymbs of an average of 3 flowers and a terminal flower.

*Inflorescence size.*—Up to 20 cm in height and 4.5 cm in width in full bloom.

*Inflorescence number.*—An average of 10 per plant 2 years in age.

*Flower fragrance.*—None detected.

*Flower quantity.*—Average of 300 flowers per flowering stem 20 cm in length.

*Flower lastingness.*—Average of 4 days per flower, individual panicles blooms for about 3 weeks, flowers persistent.

*Flower buds.*—Broadly elliptic in shape, an average of 1.5 mm in diameter and 2 mm in depth, N77D in color with apex 11C.

*Flower aspect.*—Held primarily outward on pedicels held nearly horizontal to rachis.

*Flower type.*—Campanulate.

*Flower size.*—About 1.5 mm in diameter and 6 mm in depth.

*Petals.*—About 5, implanted in hypanthium at base and narrowly elliptic in shape, margin is entire, apex is narrowly apiculate, upper and lower surface is glabrous, color of upper and lower surface when opening and mature is NN159A, about 2 mm in length and 0.3 mm in width.

*Calyx.*—Campanulate in shape, sepals fused to hypanthium, 1.8 mm in depth and diameter.

*Sepals.*—5, about 1.8 mm in length and 0.5 mm in width, un-fused portion is elliptic in shape, margin is entire, apex is broadly acute, base is fused, upper and lower surface is densely covered with hairs about 155A in color, color of upper and lower surface; base 148B, mid region N77B and apex 147A.

*Bracts.*—1, at base of peduncle, lanceolate in shape with 2 lateral and one terminal foliaceous appendages, N77A in color, an average of 5 mm in length and 2 mm in width, acute-leafy apex, base truncate and fused to peduncle.

*Peduncles.*—Average of 1 cm in length and an average of 0.7 mm in width, held nearly horizontal to rachis, N77A in color.

*Pedicels.*—Average of 2 mm in length and 0.3 mm in width, N77A in color, slightly puberulent surface, terminal is straight from peduncle and laterals are held at about a 45° angle.

*Rachis (flower scape).*—Average of 36 cm in length and an average of 2 mm in width, N186B in color, surface is sparsely covered with hairs about 0.7 mm in length, peduncle internode length is an average of 1 cm, with inflorescence commencing about 17 cm from base.

Reproductive organs:

*Gynoecium.*—2 Pistils, club-shaped, about 4 mm in length, stigmas minute and about 11D in color, styles are about 4 mm in length and N77B in color, ovaries are superior and 147B in color.

*Androcoecium.*—About 5 stamens, anthers are ovate in shape, basifixed, about 0.6 mm in diameter and 21A in color, filaments are about 3 mm in length and NN155D in color, no pollen was observed.

*Seed.*—None observed.

It is claimed:

1. A new and distinct cultivar of hybrid *Heuchera* plant named 'Blackout' as herein illustrated and described.

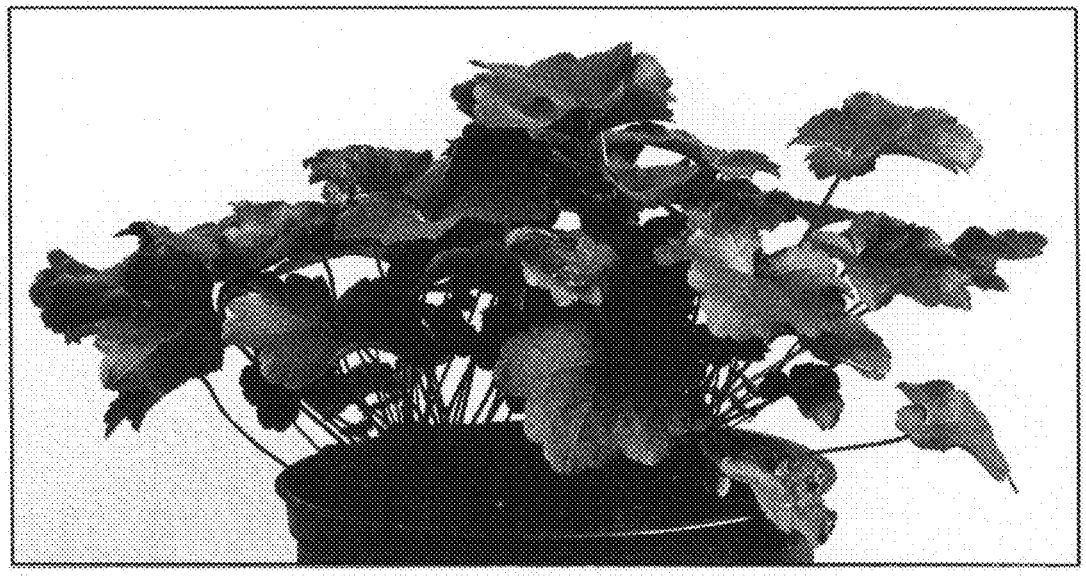

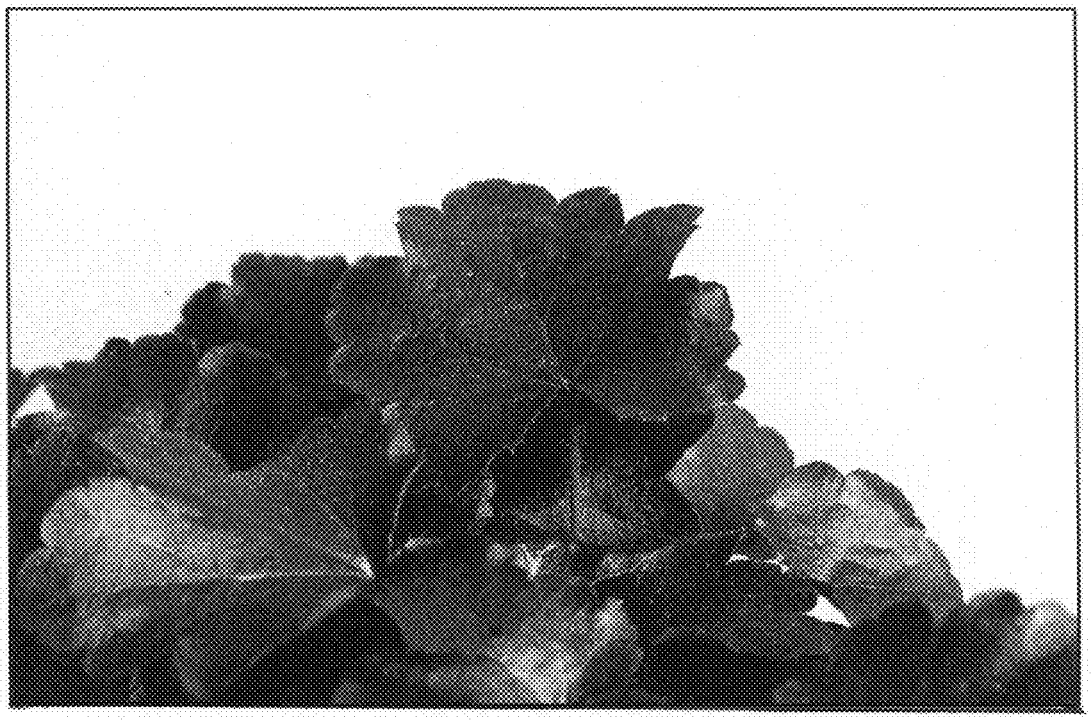

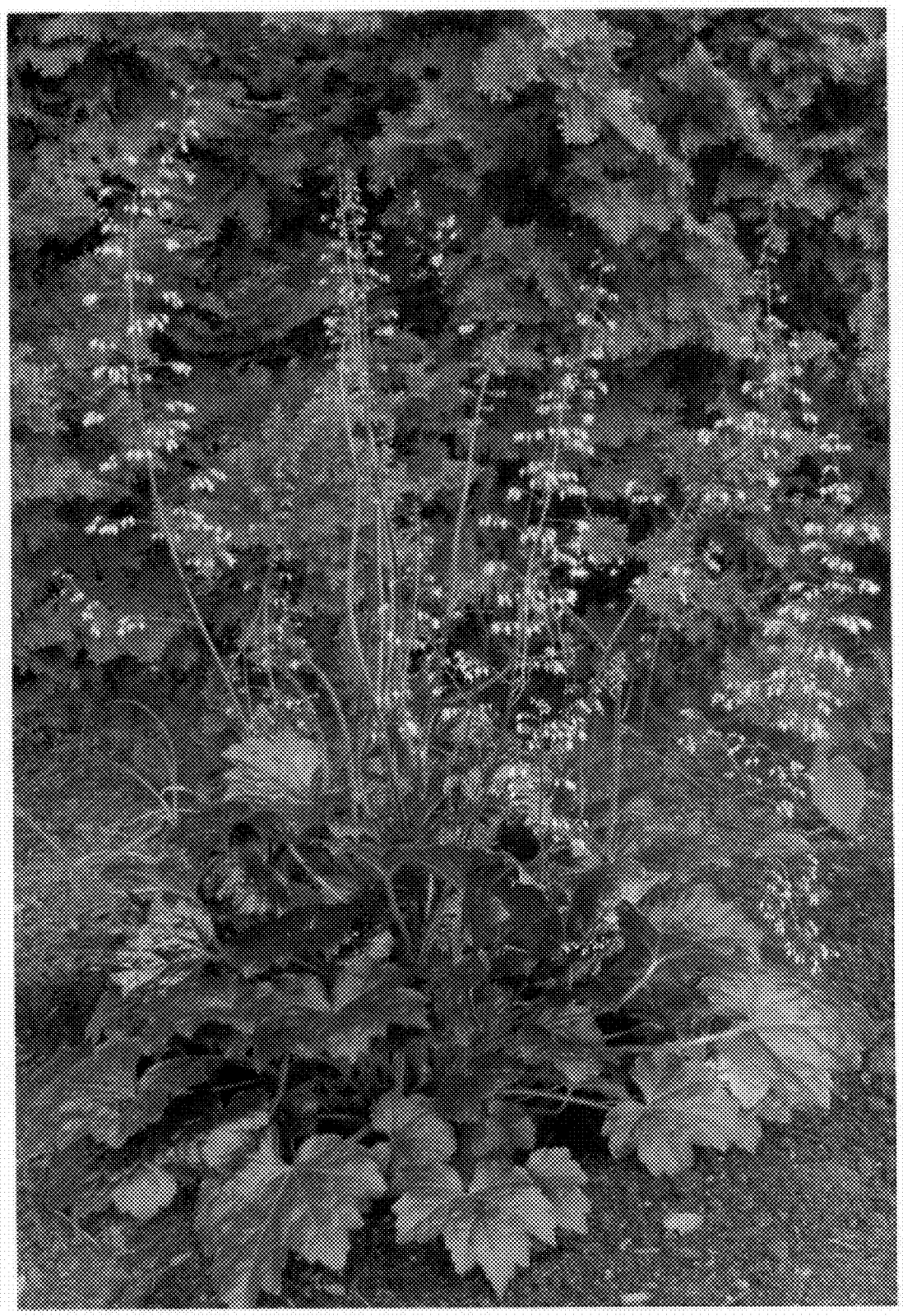

* * * * *